(12) United States Patent
Cook (10) Patent No.: US 7,780,900 B2
(45) Date of Patent: Aug. 24, 2010

(54) METHODS OF FORMING A LARYNGEAL MASK

(75) Inventor: Daniel J. Cook, St. Louis, MO (US)

(73) Assignee: Cookgas, LLC, St. Louis, MO (US)

(*) Notice: Subject to any disclaimer, the term of this patent is extended or adjusted under 35 U.S.C. 154(b) by 814 days.

(21) Appl. No.: 11/549,523

(22) Filed: Oct. 13, 2006

(65) Prior Publication Data

US 2008/0078398 A1      Apr. 3, 2008

Related U.S. Application Data

(63) Continuation-in-part of application No. 11/532,281, filed on Sep. 15, 2006.

(51) Int. Cl.
B29C 49/00    (2006.01)
A62B 18/02    (2006.01)

(52) U.S. Cl. .............. 264/523; 128/206.21; 128/207.14

(58) Field of Classification Search ................. 264/529, 264/523; 128/206.21, 207.14
See application file for complete search history.

(56) References Cited

U.S. PATENT DOCUMENTS

| | | | |
|---|---|---|---|
| 678,814 A | 7/1901 | Riggs | |
| 2,335,741 A | 11/1943 | Contaldi | |
| 2,787,010 A | 4/1957 | Uphoff | |
| 3,139,088 A | 6/1964 | Galleher, Jr. | |
| 3,434,100 A | 3/1969 | Dykzeul | |
| 3,606,669 A | 9/1971 | Kemble | |
| 3,734,100 A | 5/1973 | Walker et al. | |
| 3,756,601 A | 9/1973 | Frey et al. | |
| RE28,600 E | * 11/1975 | Lemelson | .................... 72/265 |
| 3,945,069 A | 3/1976 | Cecil | |
| 4,146,034 A | 3/1979 | Gupta | |
| 4,231,365 A | 11/1980 | Scarberry | |
| 4,327,720 A | 5/1982 | Bronson et al. | |
| 4,340,046 A | 7/1982 | Cox | |
| 4,388,076 A | 6/1983 | Waters | |
| 4,444,201 A | 4/1984 | Itoh | |
| 4,509,512 A | 4/1985 | LeClercq | |
| 4,509,514 A | 4/1985 | Brain | |
| 4,520,810 A | 6/1985 | Weiss | |
| RE31,948 E | 7/1985 | Deutsch et al. | |
| 4,540,959 A | 9/1985 | Saad | |
| 4,582,056 A | 4/1986 | McCorkle, Jr. | |
| 4,593,687 A | 6/1986 | Gray | |
| 4,661,028 A | 4/1987 | Sanger | |
| 4,674,496 A | 6/1987 | Svadijan et al. | |

(Continued)

OTHER PUBLICATIONS

"Products—LMA Fastrach," http://www.lmana.com/prod/components/products/lma_fastrach.html, printed on Jun. 19, 2005, one page.

(Continued)

*Primary Examiner*—Yogendra N Gupta
*Assistant Examiner*—Daniel Lee
(74) *Attorney, Agent, or Firm*—Lewis, Rice & Fingersh, L.C.

(57) ABSTRACT

A method for constructing a supraglottic airway of the type used to facilitate lung ventilation and the insertion of endotracheal tubes or related medical instruments through a patient's laryngeal opening where the shield is constructed of a generally single-use generally blow-molded structure.

12 Claims, 12 Drawing Sheets

U.S. PATENT DOCUMENTS

| | | | |
|---|---|---|---|
| 4,751,922 A | 6/1988 | DiPietropolo | |
| 4,791,923 A | 12/1988 | Shapiro | |
| 4,825,861 A | 5/1989 | Koss | |
| 4,863,439 A | 9/1989 | Sanderson | |
| 4,872,483 A | 10/1989 | Shah | |
| 4,895,533 A | 1/1990 | Yagi et al. | |
| 4,919,127 A | 4/1990 | Pell | |
| 4,995,388 A | 2/1991 | Brain | |
| 5,024,220 A | 6/1991 | Holmgreen et al. | |
| 5,033,919 A | 7/1991 | Choe | |
| 5,037,251 A | 8/1991 | Roth | |
| 5,042,475 A | 8/1991 | LaBombard | |
| 5,071,413 A | 12/1991 | Utterberg | |
| 5,197,463 A | 3/1993 | Jeshuran | |
| 5,218,970 A | 6/1993 | Turnbull et al. | |
| 5,222,487 A | 6/1993 | Carr et al. | |
| 5,253,658 A | 10/1993 | King | |
| 5,277,178 A | 1/1994 | Dingley | |
| 5,279,610 A | 1/1994 | Park et al. | |
| 5,282,464 A | 2/1994 | Brain | |
| 5,303,697 A | 4/1994 | Brain | |
| 5,324,080 A | 6/1994 | McNaughton et al. | |
| 5,326,196 A | 7/1994 | Noll | |
| 5,340,165 A | 8/1994 | Sheppard | |
| 5,355,879 A | 10/1994 | Brain | |
| 5,391,248 A | 2/1995 | Brain | |
| 5,392,774 A | 2/1995 | Sato | |
| 5,393,101 A | 2/1995 | Matkovich | |
| 5,477,852 A | 12/1995 | Landis et al. | |
| 5,509,408 A | 4/1996 | Kurtis | |
| 5,513,627 A | 5/1996 | Flam | |
| 5,527,316 A | 6/1996 | Stone | |
| 5,529,582 A | 6/1996 | Fukuhara | |
| 5,545,048 A | 8/1996 | Maeda | |
| 5,546,937 A | 8/1996 | Stuart et al. | |
| 5,562,371 A | 10/1996 | Reed | |
| 5,562,673 A | 10/1996 | Koblish et al. | |
| 5,569,222 A | 10/1996 | Haselhorst et al. | |
| 5,579,762 A | 12/1996 | Lee | |
| 5,584,290 A | 12/1996 | Brain | |
| 5,588,424 A | 12/1996 | Insler et al. | |
| 5,590,643 A | 1/1997 | Flam | |
| 5,623,921 A | 4/1997 | Kinsinger et al. | |
| 5,632,271 A | 5/1997 | Brain | |
| 5,643,174 A | 7/1997 | Yamamoto et al. | |
| 5,653,231 A | 8/1997 | Bell | |
| 5,655,519 A | 8/1997 | Alfery | |
| 5,682,880 A | 11/1997 | Brain | |
| 5,711,296 A | 1/1998 | Kolobow | |
| 5,713,348 A | 2/1998 | Pell | |
| 5,720,749 A | 2/1998 | Rupp | |
| 5,743,258 A | 4/1998 | Sato et al. | |
| 5,772,643 A | 6/1998 | Howell et al. | |
| 5,787,879 A | 8/1998 | Gibson | |
| 5,878,745 A | 3/1999 | Brain | |
| 5,881,726 A | 3/1999 | Neame | |
| 5,896,858 A | 4/1999 | Brain | |
| 5,937,860 A | 8/1999 | Cook | |
| 5,947,120 A | 9/1999 | Bailey | |
| 5,961,489 A | 10/1999 | Hirota | |
| 5,979,445 A | 11/1999 | Neame et al. | |
| 6,021,779 A | 2/2000 | Pagan | |
| 6,050,264 A * | 4/2000 | Greenfield | 128/207.15 |
| 6,196,224 B1 | 3/2001 | Alfery | |
| 6,240,922 B1 | 6/2001 | Pagan | |
| 6,261,401 B1 | 7/2001 | Pagan | |
| 6,374,827 B1 | 4/2002 | Bowden et al. | |
| 6,386,199 B1 | 5/2002 | Alfery | |
| 6,422,239 B1 | 7/2002 | Cook | |
| 6,450,164 B1 | 9/2002 | Banner et al. | |
| 6,604,525 B2 * | 8/2003 | Pagan | 128/207.15 |
| 6,612,305 B2 | 9/2003 | Fauza | |
| 6,631,720 B1 | 10/2003 | Brain | |
| 6,668,821 B2 | 12/2003 | Christopher | |
| 6,705,318 B1 | 3/2004 | Brain | |
| 6,705,320 B1 | 3/2004 | Anderson | |
| 6,705,321 B2 | 3/2004 | Cook | |
| 6,705,322 B2 | 3/2004 | Chang | |
| 6,729,325 B2 | 5/2004 | Alfery | |
| 6,892,731 B2 | 5/2005 | Cook | |
| 6,899,147 B2 | 5/2005 | Ogawa et al. | |
| 6,923,176 B2 | 8/2005 | Ranzinger | |
| 6,935,153 B2 | 8/2005 | Frigo et al. | |
| 6,983,744 B2 | 1/2006 | Alfery | |
| 7,013,899 B2 | 3/2006 | Alfery et al. | |
| 7,021,686 B2 | 4/2006 | Glasgow et al. | |
| 7,040,312 B2 | 5/2006 | Alfery et al. | |
| 7,040,322 B2 | 5/2006 | Fortuna | |
| 7,096,868 B2 | 8/2006 | Tateo et al. | |
| 7,097,802 B2 | 8/2006 | Brain | |
| 7,128,071 B2 | 10/2006 | Brain | |
| 1,345,425 A1 | 3/2008 | Wells | |
| 2001/0050082 A1 | 12/2001 | Christopher | |
| 2004/0020491 A1 | 2/2004 | Fortuna | |
| 2004/0079364 A1 | 4/2004 | Christopher | |
| 2005/0016529 A1 * | 1/2005 | Cook | 128/200.24 |
| 2005/0051173 A1 | 3/2005 | Brain | |
| 2005/0139220 A1 | 6/2005 | Christopher | |
| 2006/0027238 A1 | 2/2006 | Lin | |
| 2006/0076021 A1 | 4/2006 | Chang | |
| 2006/0180156 A1 | 8/2006 | Baska | |
| 2006/0207597 A1 | 9/2006 | Wright | |
| 2007/0028923 A1 | 2/2007 | Souris et al. | |
| 2007/0102001 A1 | 5/2007 | Brain | |
| 2007/0137651 A1 | 6/2007 | Glassenberg et al. | |
| 2007/0246050 A1 | 10/2007 | Parikh et al. | |
| 2008/0078398 A1 | 4/2008 | Cook | |

OTHER PUBLICATIONS

"9c Removal of LMA-Fastrach Prior to Extubation," LMA-Fastrach Instructional Manual, www.Imana.com/docs/fastrach_instruction.pdf, Feb. 2002, pages cover (2 pages), 26-27.

Byrd, Jr., R.P."Ventilation, Mechanical," http://www.emedicine.com/med/topic3370.htm, Jul. 6, 2006, pp. 1-13.

"Ambu Product Information," Ambu A/S, 2007, pp. 1-18, Denmark.

"Intersurgical Complete Respiratory Systems," http://www.intersurgical.com/productscatalog/choosegroup.aspx?cm..., printed on Apr. 11, 2007, one page.

"LMA Airway Instruction Manual," The Laryngeal Mask Company Limited, www.Imana.com/docs/LMA_Airways_Manual.pdf, 2005, pp. 1-23.

International Search Report, International Patent Application No. PCT/US2008/060425, mailed Sep. 29, 2008, 11 pages.

* cited by examiner

METHODS OF FORMING A LARYNGEAL MASK

CROSS REFERENCE TO RELATED APPLICATION(S)

This application is a Continuation-in-part of and claims priority to U.S. patent application Ser. No.: 11/532,281, filed Sep. 15, 2006 and currently pending, the entire disclosure of which is herein incorporated by reference.

BACKGROUND

1. Field of the Invention

The invention relates to methods of making artificial airway devices, more specifically to methods of making supraglottic airways utilizing blow molding techniques 2. Description of Related Art In general, supraglottic airways such as laryngeal masks allowing for both rapid lung ventilation and the insertion of medical instruments and tubes into the laryngeal openings of patients have been described in patents, such as U.S. Pat. No. 4,509,514 to Brain and U.S. Pat. Nos. 6,422,239 and 5,937,860 to Cook the entire disclosures of which are herein incorporated by reference. Laryngeal masks generally consist of two major components, a breathing tube and an inflatable shield, these devices are inserted into a patient's throat, and when properly positioned, cover the laryngeal opening. A seal is then formed around the circumference of the laryngeal opening by the inflation of a ring-like structure located toward the front of the mask (patient end). Inflation of the ring exerts pressure against the front, sides, and rear portions of the oropharynx, securing the device in place such that the laryngeal opening is positioned in alignment with a recessed cavity in the mask face. Extending from a point external to the oral cavity, the flexible breathing tube terminates within the recessed cavity, aligned axially with the laryngeal opening. The positioning of the flexible breathing tube allows the passage of endo-tracheal tubes or related medical instruments into the laryngeal opening, in addition to allowing for lung ventilation.

Supraglottic airways of this type are typically manufactured by one of two methods. One method involves forming the upper and lower portions of the inflatable peripheral portion of the mask and the base separately using various molding techniques. The two portions are then connected using heat, pressure, adhesive, or combinations of each. While this method has been successful, the parts must be glued together meaning that several process steps are necessary to manufacture a market-ready product and second, the later join results in a seam which results in a point of potentially compromised stability.

Supraglottic airways of this type have also been manufactured using injection molds including cores as discussed in U.S. patent application Ser. No. 10/691,399 the entire disclosure of which is herein incorporated by reference. While these methods have also been successful, they are often more expensive and slower than other molding techniques.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein are methods to construct a supraglottic airway, specifically a laryngeal mask airway, primarily intended to facilitate lung ventilation and the insertion of endo-tracheal tubes or related medical instruments into a patient's trachea as needed during general anesthesia, intensive care, critical patient care, or at any other time that ventilation would be desired. In a laryngeal mask embodiment of such a supraglottic airway, the mask comprises a flexible ventilation tube and an inflatable positioning shield generally conforming to the anatomy of the oropharynx region surrounding the laryngeal opening, and securely affixed to the distal end of the ventilation tube. The shield is preferably constructed of a single piece such as by utilizing blow-molding techniques that produce walls of varying thickness depending on the portion of the shield. This provides for a more robust and useful device. A tube is then attached thereto along with the inflation pump to provide for a device of relatively simple assembly.

Described herein, among other things, is a method for constructing a laryngeal mask airway comprising; providing a respiratory tube having a distal end, a proximal end, and a length there between; forming a shield comprising an inflatable outer ring and a posterior base wherein said shield is formed as a single hollow balloon having an entry point at a proximal end, the shield having two opposing surfaces of the hollow balloon pushed together and attached to form said posterior base, the remaining structure encircling said posterior base forming said outer ring, the posterior base being the base of a recessed cavity and the outer ring surrounding said recessed cavity; cutting a hole into said outer ring in an area adjacent said posterior base; threading said respiratory tube through said hole and said entry point so that the distal end of said respiratory tube is placed adjacent said posterior base in said recessed cavity; and adhering said respiratory tube to said shield in such manner that air can pass through said respiratory tube from said proximal end, to said distal end without entering said outer ring.

In an embodiment of the method the respiratory tube is smoothly curved and the airway may be intended to be disposed of after a single use.

In an embodiment of the method the step of forming comprises blow molding said shield. The shield may then further include a connection nozzle on said proximal end, which is removed and discarded prior to said threading.

In another embodiment, the respiratory tube includes a wedge section which may include a wedge, a groove, and a raised disk so that the wedge is positioned within said recessed cavity when said shield, said respiratory tube, and said inflation tube are adhered together.

There is also described herein, a method for constructing a laryngeal mask airway comprising, providing a respiratory tube having a distal end, a proximal end, and a length there between; forming a shield comprising an inflatable outer ring and a posterior base wherein said shield is formed as a single hollow balloon having an entry point at a proximal end, the shield having two opposing surfaces of the hollow balloon pushed together and attached to form said posterior base, the remaining structure encircling said posterior base forming said outer ring, the posterior base being the base of a recessed cavity and the outer ring surrounding said recessed cavity, said posterior base being more than twice as thick as said remaining structure forming said outer ring; and attaching said respiratory tube to said shield to form said laryngeal mask airway.

In an embodiment of the method the respiratory tube is smoothly curved and the airway may be intended to be disposed of after a single use.

In an embodiment of the method the step of forming comprises blow molding said shield. The shield may then further include a connection nozzle on said proximal end, which is removed and discarded prior to said threading.

In another embodiment of the method, said step of attaching comprises cutting a hole into said outer ring in an area adjacent said posterior base; threading said respiratory tube through said hole and said entry point so that the distal end of said respiratory tube is placed adjacent said posterior base in said recessed cavity; and adhering said respiratory tube to said shield in such manner that air can pass through said respiratory tube from said proximal end, to said distal end without entering said outer ring.

In another embodiment, the respiratory tube includes a wedge section which may include a wedge, a groove, and a raised disk so that the wedge is positioned within said recessed cavity when said shield, said respiratory tube, and said inflation tube are adhered together There is also described herein, a method for constructing an inflatable supraglottic airway comprising; providing a respiratory tube having a distal end, a proximal end, and a length there between; blow-molding an inflatable part of said supraglottic airway using an ovalized tool, having at least one point of ovalization, said tool produces a wall thickness in at least one first portion that is thicker than a wall thickness in a second portion; and attaching said respiratory tube to said inflatable part to form said inflatable supraglottic airway.

In an embodiment of the method, said at least one first portion comprises at least two first portions and said at least one point of ovalization comprises at least two points of ovalization.

There is also described herein, a method of constructing a shield for a laryngeal mask airway; the method comprising: providing an ovalized tool having two points of ovalization which interacts with a mold for a shield of a laryngeal mask airway, said mold including a hollow chamber for forming said shield; aligning said ovalized tool so that said two points are arranged to feed material to portions of said hollow chamber which correspond to at least a portion of a posterior base of a shield; blow molding said shield, said shield comprising an inflatable outer ring formed of a single layer of material and a posterior base formed of at least a double layer of material each of said layers of said double layer of material being thicker than said single layer of material in said inflatable outer ring; and cutting a hole through a portion of said outer ring adjacent said posterior base.

DESCRIPTION OF THE PREFERRED
EMBODIMENT(S)

The following detailed description illustrates by way of example and not by way of limitation. Described herein, among other things, are embodiments of methods for constructing supraglottic airways using blow molding. Specifically, the supraglottic airway has a shield (201) constructed as a single blow-molded structure to allow for improved ease of assembly and speed of manufacture. While the supraglottic airway described herein incorporates certain features in the shape and features of the shield (201) for improved placement in the airway, it should be recognized that these features are not required and the techniques of manufacture can be used on airways of other shapes and forms.

Figure 1:
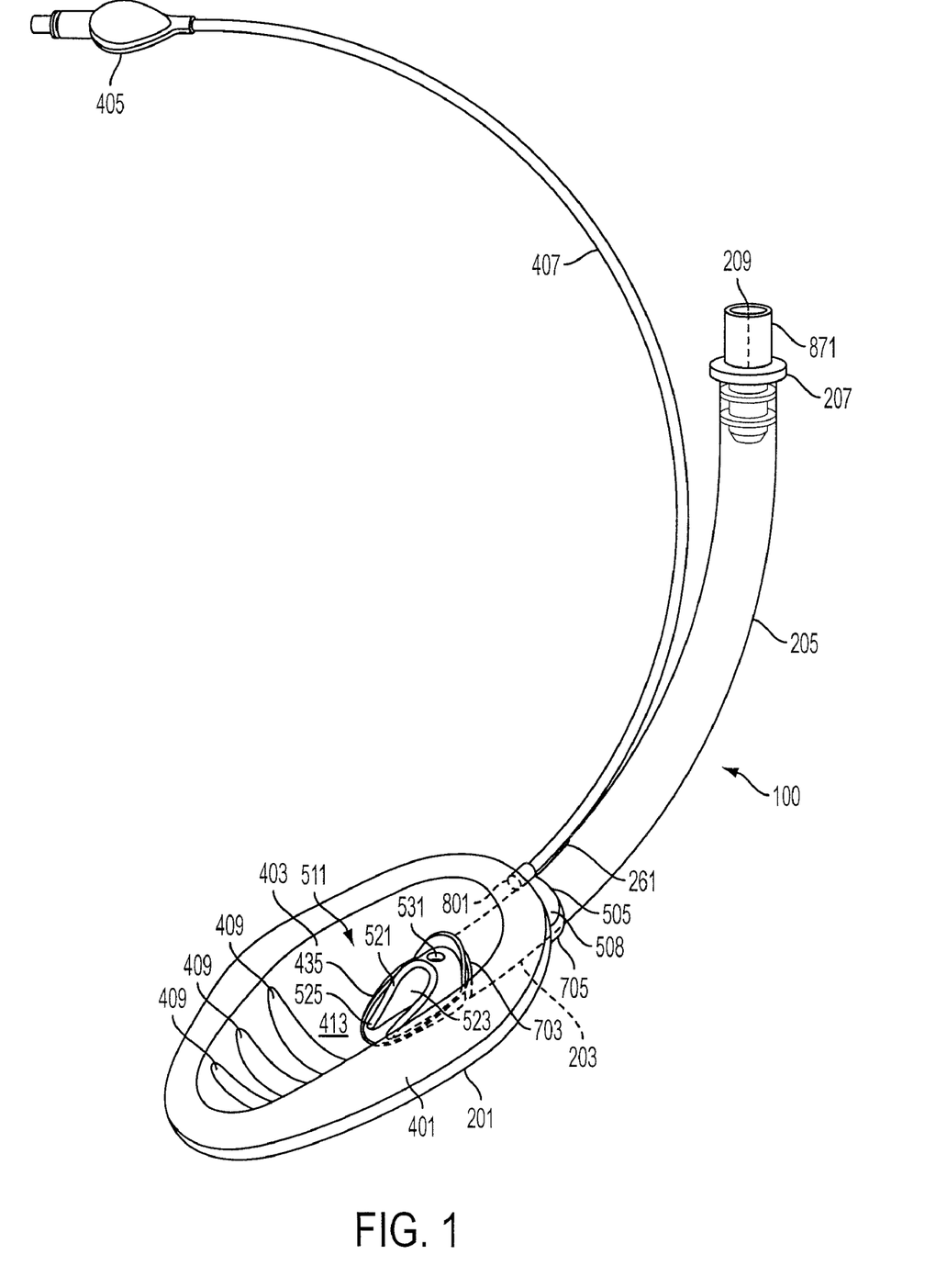
FIG. 1 shows a perspective view of an embodiment of a laryngeal mask as assembled.

FIG. 1 provides for an embodiment of a supraglottic airway in the form of removable laryngeal mask airway (100). This mask (100) is chosen as an exemplary form of supraglottic airway to simply demonstrate how the systems and methods of construction and assembly discussed herein can be used. It is in no way intended to be descriptive of all airways which may be used in other embodiments. In the depicted embodiment, the laryngeal mask (100) generally comprises four major components. There is an inflatable positioning shield (201) which is secured toward the distal end (203) of a respiratory tube (205) formed into an arcuate curve. There is also an inflation pump (405) and inflation tube (407) designed to provide for inflation and deflation of at least a portion of the shield (201) and a connector (871). The laryngeal mask (100) is generally composed of a relatively soft flexible material such as, but not limited to, silicone-rubber polymer or plastics.

The inflatable positioning shield (201) is constructed, in the depicted embodiments, by blow molding. The shield (201) comprises a generally wedge-shaped ellipsoid, ovoid, or toroid outer ring (401) with a pliable molded posterior base (403) attached thereto so that the posterior base (403) forms the base of, and the outer ring (401) surrounds, a recessed cavity (511). The outer ring (401) is preferably repeatedly inflatable and deflatable with such inflation being accomplished by attachment of an inflation device or pump (405) which is capable of pulling air from the ambient, into an inflation tube (407) and from there into the interior of the outer ring (401). The outer ring (401), when inflated, is sized and shaped to generally conform to the approximate available space in the oropharynx region.

The posterior base (403) is secured longitudinally within the hole in the center of the outer ring (401). The posterior base (403) is generally molded in a fashion to form an elongated and tapered hemisphere relative the generally major plane of the outer ring (401) so as to give the shield (201) an overall shape such as that seen in the FIGS. In the depicted embodiment, there are semi-rigid raised ridges (409) positioned longitudinally parallel to each other along the surface (413) of the posterior base (403) "inside" the hole of the outer ring (401).

The shield (201), may be molded through blow molding techniques to provide for a single piece construction to which the other components which are separately constructed may be attached. In blow molding, the shield outer ring (401) and posterior base (403) are formed by blowing the structure into a shaped mold such as that shown in FIGS. 7-12. As opposed to in traditional blow-molding, however, where the wall thickness of various portions of the shield are forced to be of generally identical width, the mold of FIGS. 7-12, or another mold if a different shape of shield (201) is desired may be used in conjunction with an ovalized extrusion tool (801) such as that shown in FIGS. 13-14 to allow the shield (201) to have different portions produced at different thicknesses. In a preferred embodiment, this allows the posterior base (403) to be formed with a resultant thickness more than twice that of the thickness of the structure of the outer ring, by increasing the thickness of either or both of upper portion (402) and lower portion (404). This in turn provides improved resiliency and strength to the shield (201) which previously had to be provided by attachment of a reinforcing component adhered to the posterior base (403).

Figure 3:
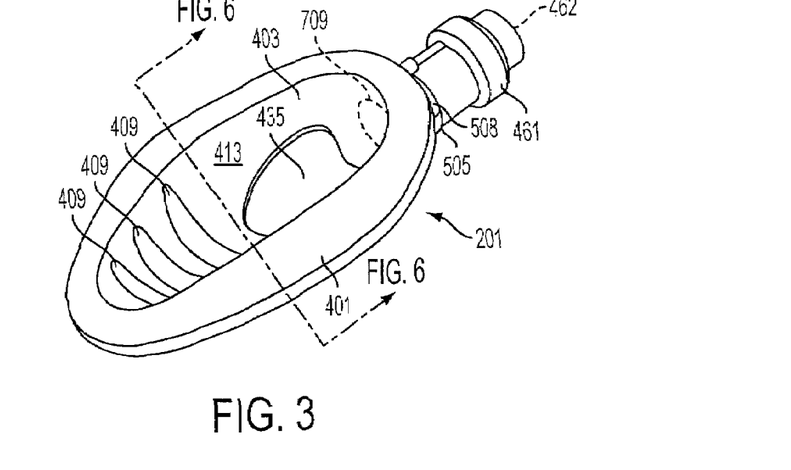
FIG. 3 shows a perspective view of a shield that has been blow-molded and not yet trimmed.

As can be seen in FIG. 3, the shield when originally blow-molded accompanies a single hollow structure or "balloon." The shield (201) is formed as it appears in FIG. 1 but further includes a connection nozzle (461) attached to the proximal end (505). The connection nozzle (461) is the original source of material for the blow-molding and will be removed and discarded, however it serves to initially define an entry point (462) to the interior of the balloon which will be used to form the shield (201).

Figure 6:
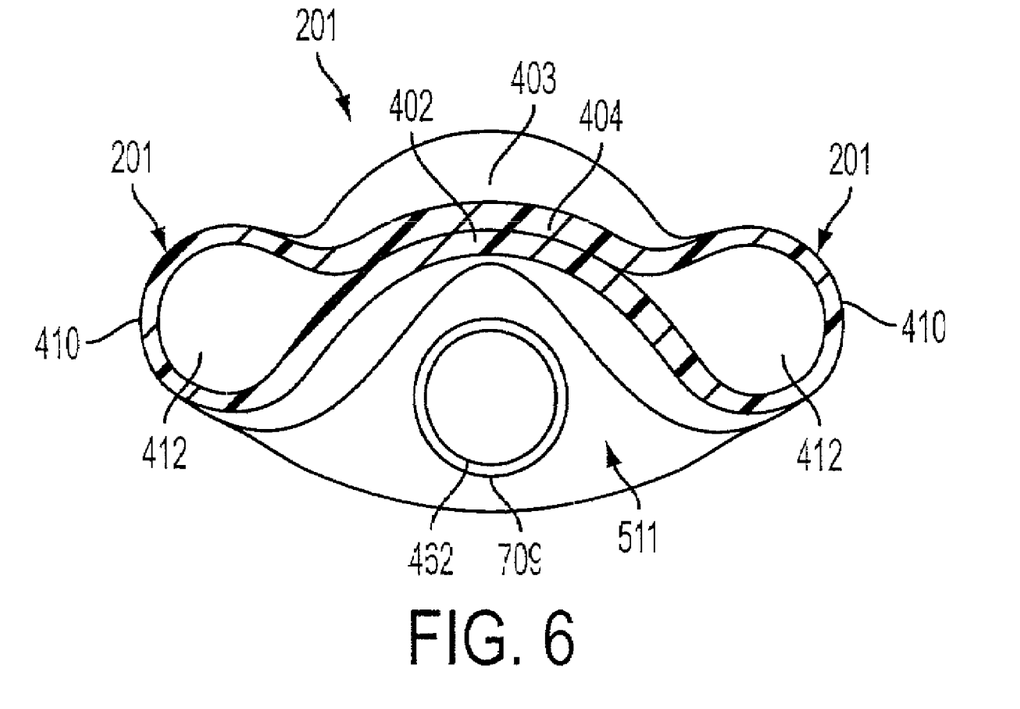
FIG. 6 shows a cut-through along line 6-6 in FIG. 3.
Figure 7:
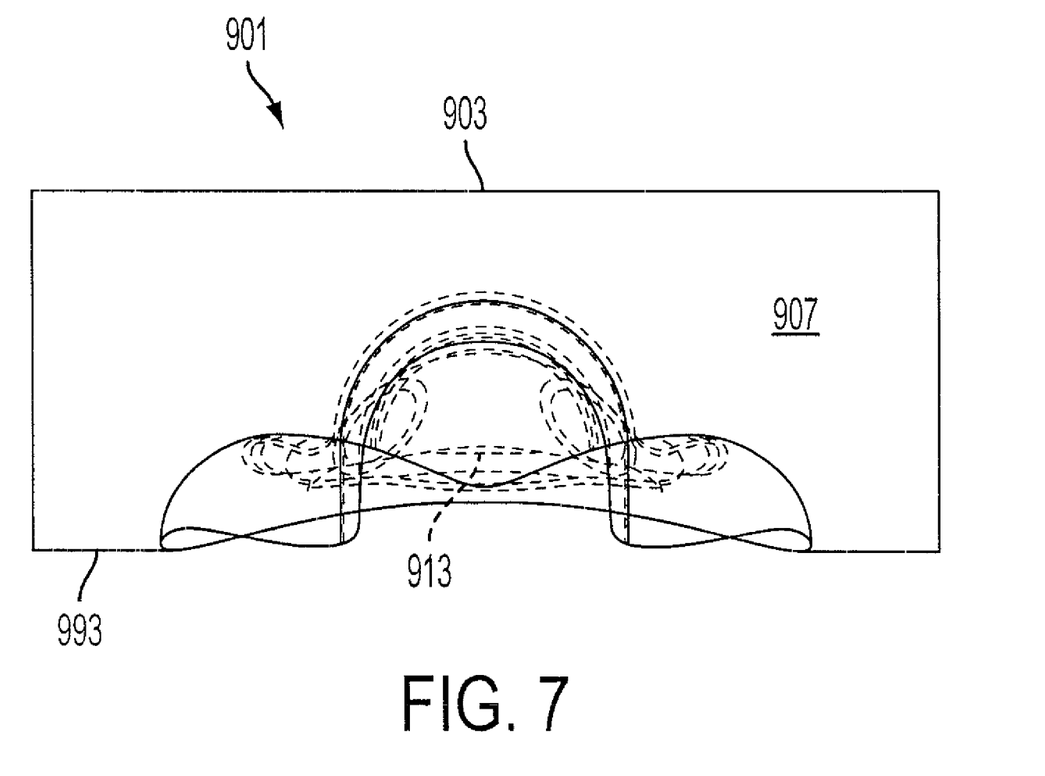
FIG. 7 shows an end on view of the bottom half of a blow-mold which may be used to produce an embodiment of a shield, such as that shown in FIG. 3.
Figure 8:
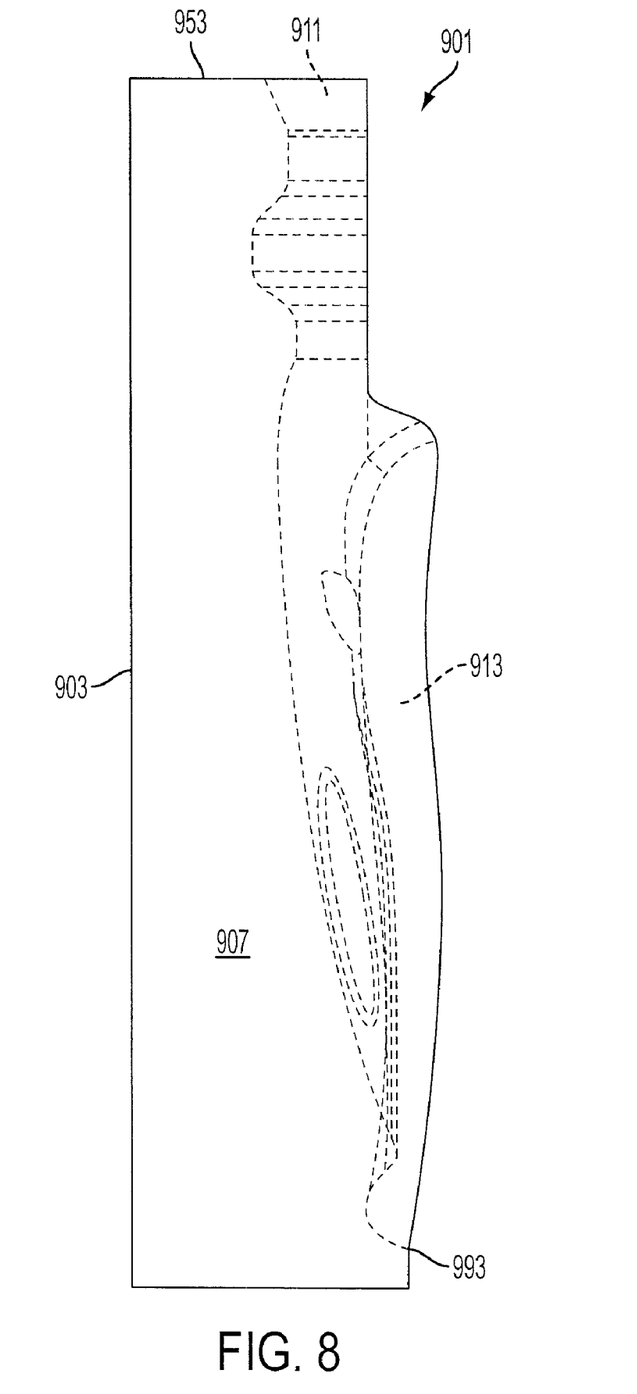
FIG. 8 shows a side view of the bottom half of the blow-mold of FIG. 7.
Figure 9:
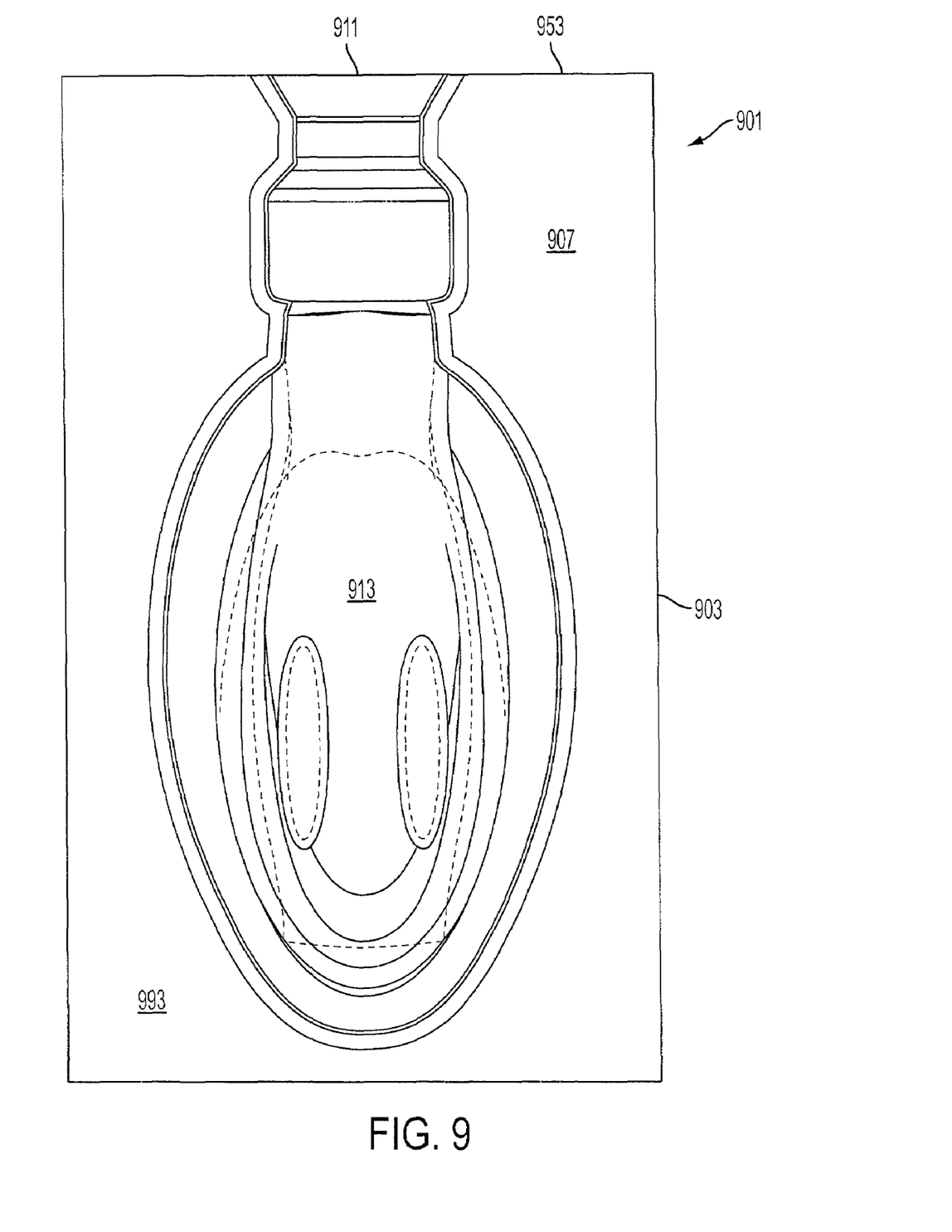
FIG. 9 shows a top view of the bottom half of the blow-mold of FIG. 7.
Figure 10:
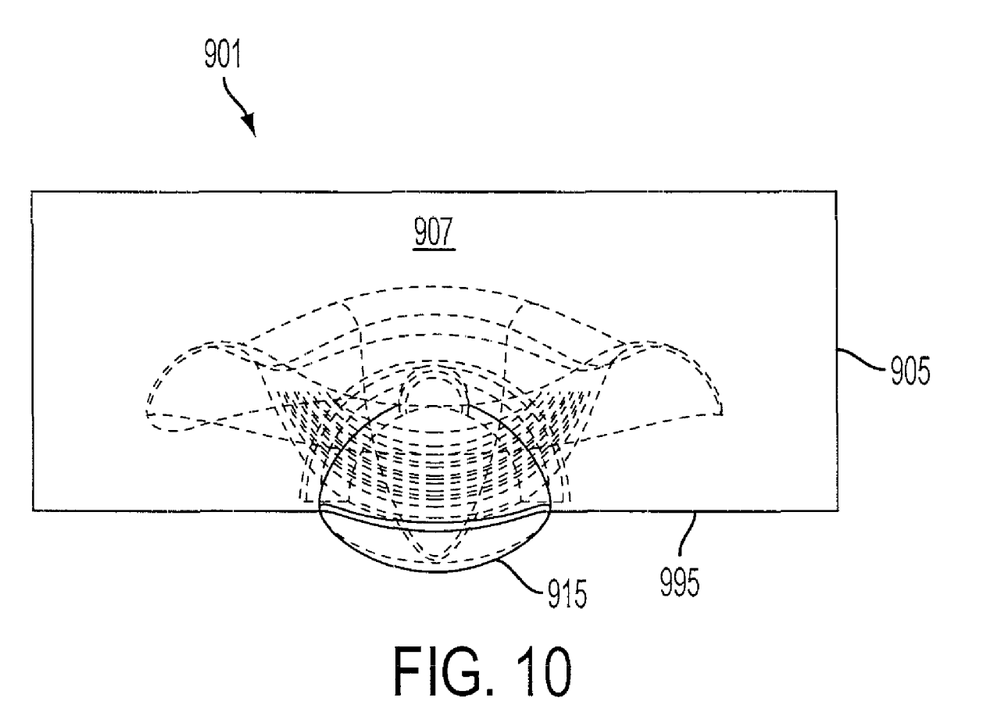
FIG. 10 shows a front view of the top half of the blow-mold of FIG. 7.
Figure 11:
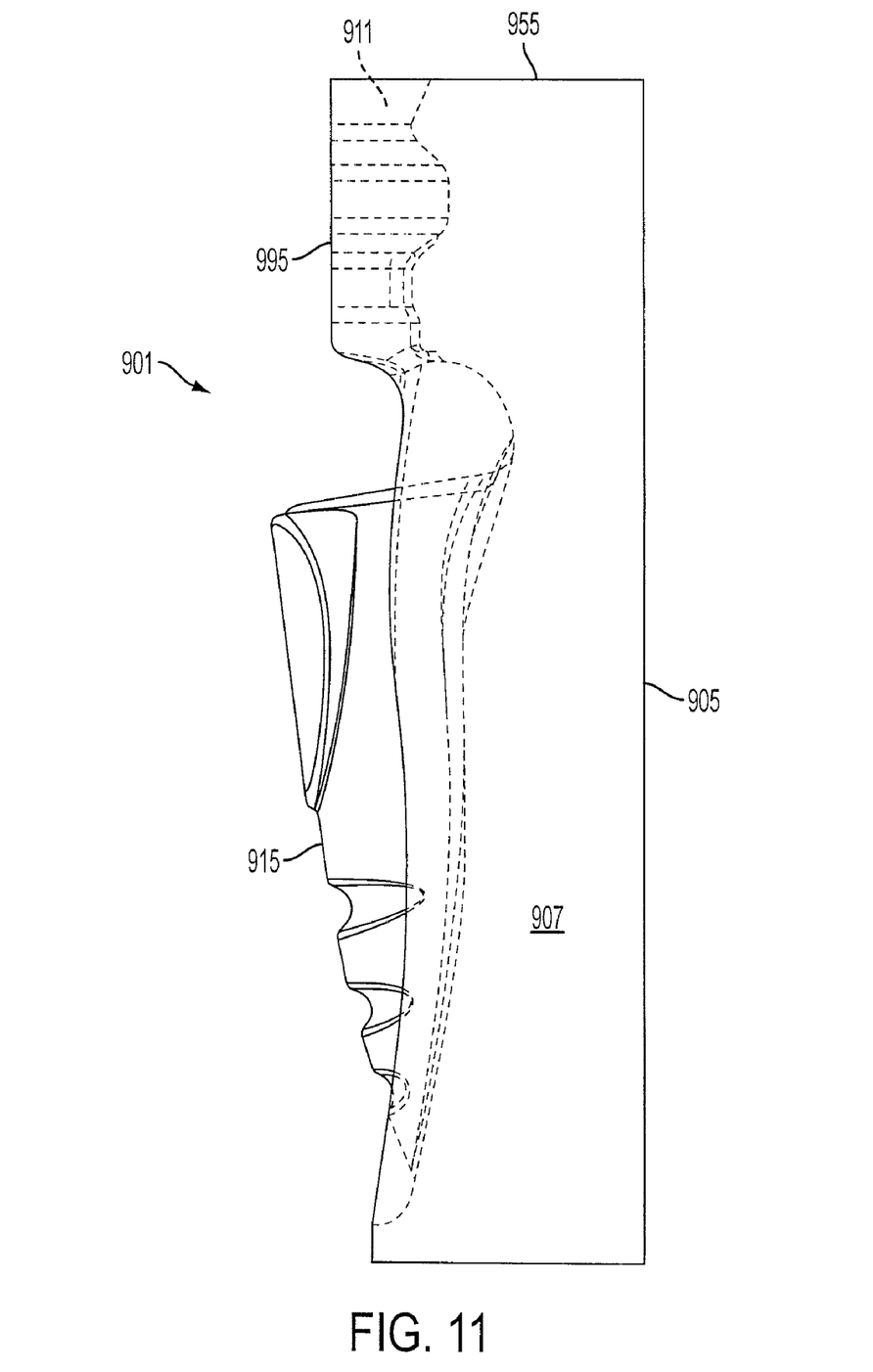
FIG. 11 shows a side view of the top half of the blow-mold of FIG. 10.
Figure 12:
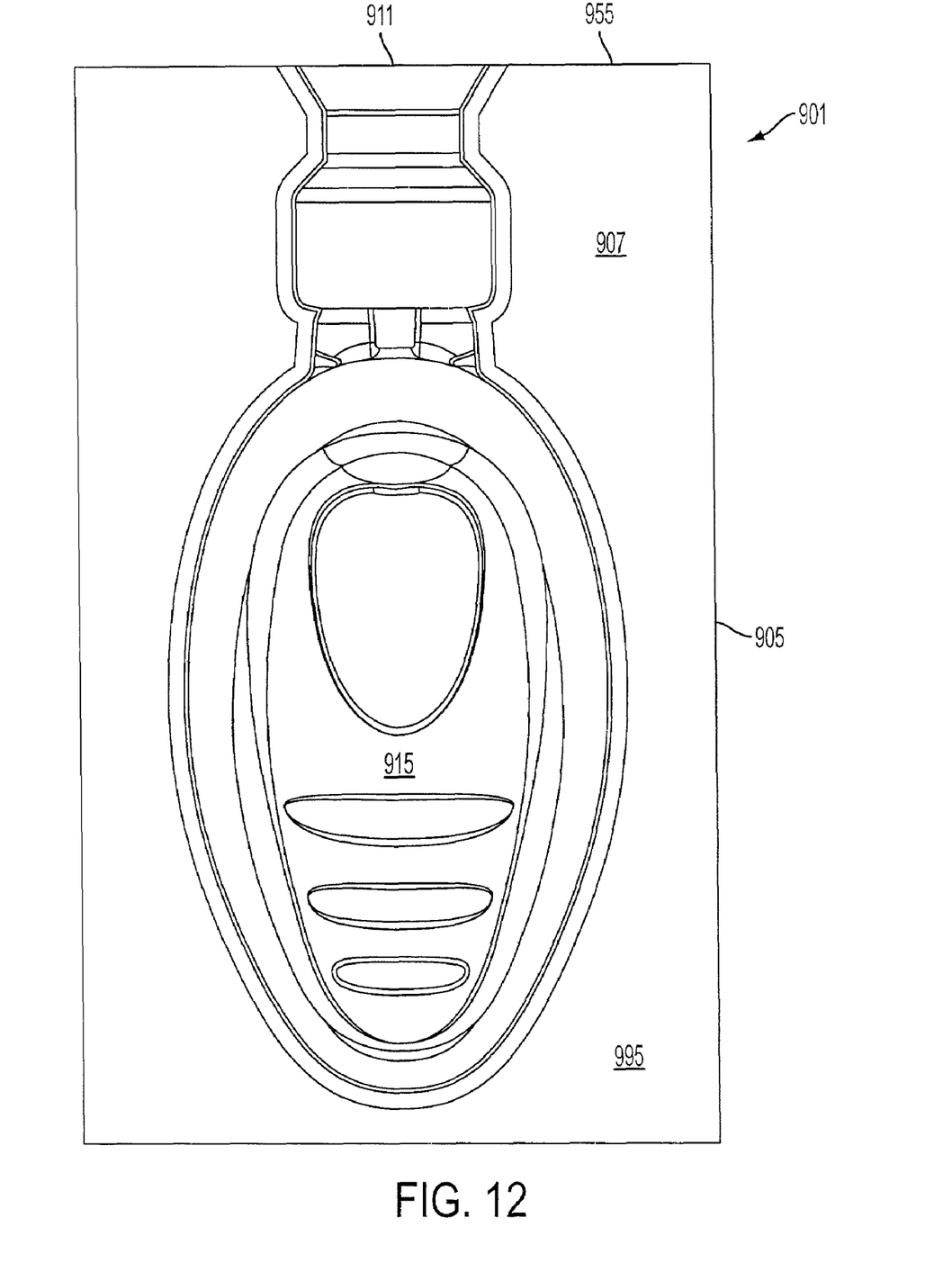
FIG. 12 shows a bottom view of the top half of the blow-mold of FIG. 10.

Blow-molding techniques generally require that the structure to be formed comprise a hollow balloon which is then pushed or molded into shape. FIG. 3 shows the appearance of the outer surface of the balloon when molded into a shield (201). FIG. 6 shows a cross-section of the shield of FIG. 3 indicating how the shield (201) is preferably constructed to indicate how the balloon is compressed and formed into the desired structure shown in FIG. 3. As can be seen in FIG. 6, the outer ring (401) and posterior base (403) are formed by taking the opposing sides of the balloon and partially pushing them together at an interior location so that they touch at a point spaced from the entry point (462) and the neck (508). These opposing sides are then adhered together either through the use of an adhesive or simply through the adhesive capabilities of the material being formed so as to form the posterior base (403) and outer ring (401) as shown in the FIGS. As should be apparent, this style of formation results in a structure whereby the outer ring (401) forms a generally toroidal structure as discussed previously including a hollow (412) and the posterior base (403) does not allow for air passage between the two surfaces which form its upper (402) and lower (404) portions thereby forming a generally solid base attached to the outer ring (401) and resulting in the "dish" shape of FIG. 3. Further, while the structure will usually include adhesion points, these are generally internal to outer ring (401) and only used to connect the wedge (501) to the shield (201) and therefore are not particularly stretched by inflation and failure does not result in deflation or failure of the shield (201) outer ring (411).

As can be further seen in FIG. 6, each half (402) and (404) of the posterior base (403) is thicker than either of the outer surfaces (410) of the outer ring (401) which provides additional strength to the shield (201) as a whole. At the same time, however, the structure is not rigid and is capable of bending during insertion. In a preferred embodiment, the outer surfaces (410) are in fact molded to be significantly thinner than each of the upper portion (402) and lower portion (404) to provide for even more strength to the posterior base (403).

FIGS. 7-12 provide for various drawings of a mold (901), specifically a blow-molding mold which may be used for blow molding a device such as the device of FIG. 3. The mold (901) generally comprises two halves a first or bottom half (903) and a second or top half (905). The mold generally comprises a support structure (907) which includes a void. The void is arranged so that when the two halves (903) and (905) are placed together, the two halves (903) and (905) of the mold opening form the void with an opening (911) at one end. So as to form the relatively flat shape of the shield (201) the first half of the mold (903) includes a generally recessed form (913). The second half of the mold (905) generally includes an extended form (915) which is extended into the recessed form (913) when the two halves (903) and (905) are assembled by placing the complementary faces (993) and (995) together.

As should be apparent from FIGS. 3 and 7-12, the resultant shape of the shield is therefore formed as a single hollow structure by being forced into the void between the forms (713) and (715) as shown in FIGS. 7-12 forming the shield (201) of FIG. 3.

Figure 13:
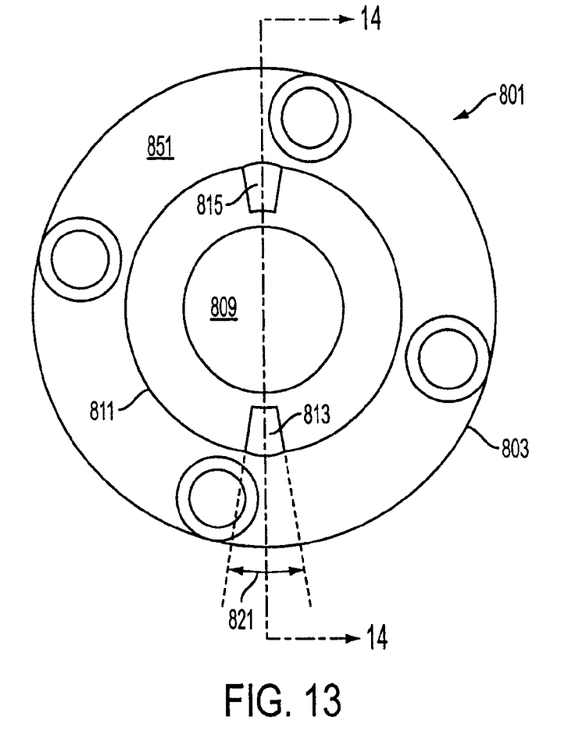
FIG. 13 shows a top view of an extension tool which can be used with the blow-mold of FIGS. 7-12.
Figure 14:
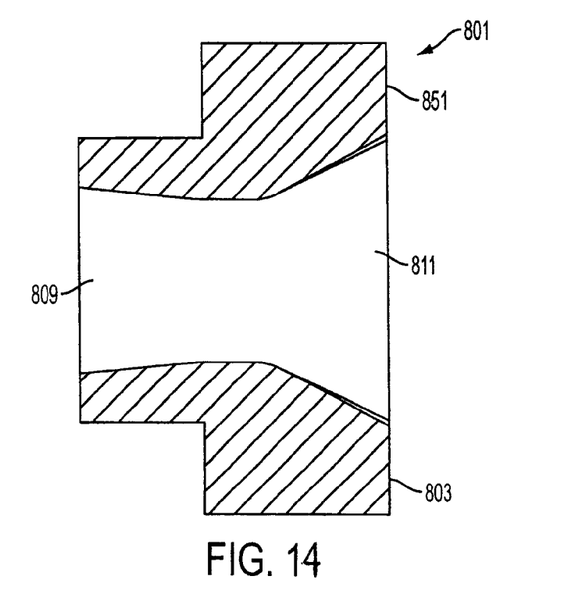
FIG. 14 shows a side view of the extrusion die of FIG. 13.

The differing of the width of different portions of the shield (201) such as outer surface (410), upper portion (402), and lower portion (404) as shown in FIG. 6 may be accomplished through the use of a shaped extrusion tool (801) for extending the material into the blow mold (901) of FIGS. 7-12. FIGS. 13-14 provide for two different views of an extrusion tool (801) which can be used to provide for a small alteration in the amount of material provided to the mold (901) at certain points in the mold (901).

Traditionally blow molding extrusion tools have included circular openings (811) and therefore as the material is blown into the mold (901), each side of the resulting structure is of generally equal width (thickness). This width can be altered by slightly elongating or "ovalizing" portions of the opening (811) providing increased extrusion material thickness for sections of the mold (901) fed by that part corresponding to the ovalization. In FIG. 13, this is best shown by the grooves (813) and (815) which are inside the circular opening (811) of the tool (801). Therefore, positions of the mold (901) which are fed by the ovalized sections of the extrusion tool (801) result in walls that are thicker than other areas.

An extrusion tool (801) used in an embodiment of a method for forming the shield (201) is shown in FIGS. 13-14. In this embodiment, the extrusion tool (801) provides a generally circular tool (803) with an inlet (809) and circular opening (811). The opening (811) includes two points (813) and (815) of ovalization. These two points (813) and (815) are aligned with the mold (901) to provide the material which will enter the mold (901) and be forced together to form posterior base (403) by the compression of upper portion (402) and lower portion (404). In particular, the two points (813) and (815) would be arranged so as to be aligned with the top and bottom sides of the mold (901) as viewed in FIGS. 7 or 10 when the tool face (851) is aligned with the top surfaces (953) and (955) of the mold (901).

It should be recognized that the ovalization need not be a huge change. In an embodiment, the oval points (813) and (815) may comprise less than 10 percent of the arc length (821) of the circle forming the ovalization, more preferably between 2 and 7 percent of the circle.

Figure 4:
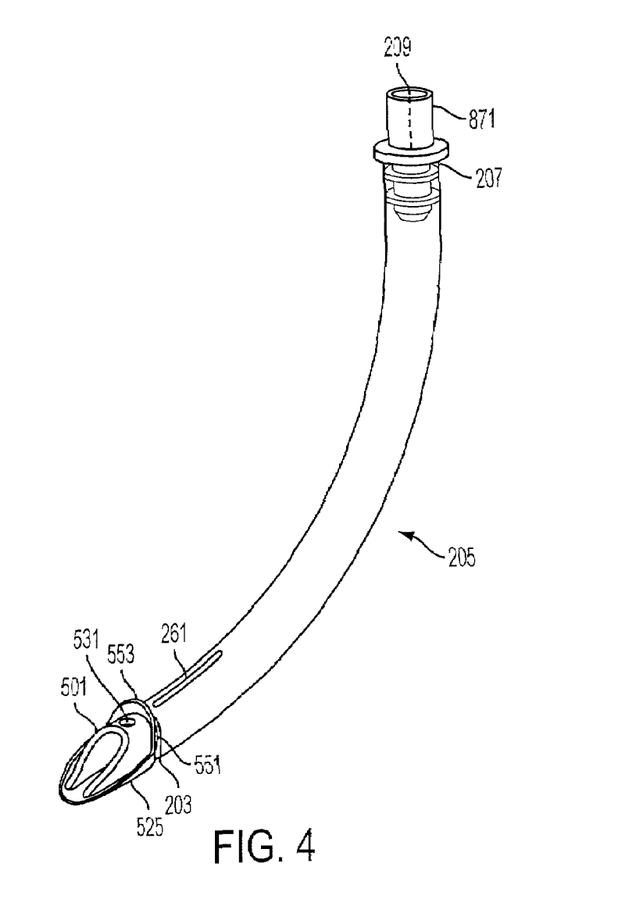
FIG. 4 shows a perspective view of a breathing tube.

Once the shield (201) is formed, it is generally connected to the respiratory tube (205) by means of a hollow wedge (501) which allows the respiratory tube (205) to pass through the shield (201) and into the recessed cavity (511) formed above the posterior base (403) and inside the "hole" of the outer ring (401). In a preferred assembly, the shield (201) as shown in FIG. 3 is attached to a respiratory tube assembly as shown in FIG. 4 In this assembly, the hollow wedge (501) is attached generally to the distal end (203) of the respiratory tube (205) as is visible in FIG. 4 and comprises a somewhat more rigid construction than the other components. The wedge (501) section may be inserted into the end of the respiratory tube (403), or may be co-molded in an alternative embodiment. The wedge (501) section preferably includes the wedge (501) as well as a groove (551) which is circumferentially arranged toward the distal end (203) of the respiratory tube (205) and a raised disk (553) placed distal of the groove (551) but proximal the wedge (501).

Once assembled, the respiratory tube (205) passes through a first airtight peripheral seal (703) to exit the recessed cavity (511) and a second airtight peripheral seal (705) towards the proximal end (505) of the inflatable positioning shield (201). The wedge (501) therefore gives an access into the shield recess (511) from the interior of the respiratory tube (205) allowing air to pass from the recessed cavity (511) into the distal end (203) of the respiratory tube (205) and from there out the proximal end (207) of the respiratory tube (205) without passing into the outer ring (401). The wedge (501) is generally formed into an angle (521) to the length of the respiratory tube (205) which is generally between 0 and 90 degrees and preferably about 30 to about 35 degrees with the posterior base (403), forming an elongated elliptically shaped distal lumen (523) open to the interior of the shield recess (511) and interior of the respiratory tube (205).

There may also be included a ventilation lumen (531) through the wedge (501) to provide an alternate airway in the event the distal lumen (523) becomes obstructed during patient lung ventilation. The ventilation lumen (531) also generally prevents the formation of a pressure differential between the recessed cavity (511) and flexible respiratory tube (205). Absent a pressure differential, any object obstructing the distal lumen (523) will not generally become inextricably lodged.

The respiratory tube (205) may be formed in any manner known to those of ordinary skill in the art but will generally form a smoothly curving hollow cylinder of generally circular or elliptical cross-section preferably approximating, for ease of insertion, the shape of the human throat. The respiratory tube (205) is preferably sized and shaped to accommodate the passage of endo-tracheal tubes and related medical devices up to 8.5 French in diameter. The length of respiratory tube (205) is such that when the laryngeal mask (100) is properly positioned for use within the oropharynx, the attachment (proximal) end (207) of respiratory tube (205) is located exterior to the oral cavity of the patient. The attachment end (207) of the respiratory tube (205) terminates in an unobstructed proximal lumen (209), providing a direct pathway through the respiratory tube (205) to the distal end (203) and distal lumen (523). In alternative embodiments, the attachment end (207) may be fitted with removable adapters or connectors (871) suitable for connection to a variety of medical devices, for example, lung ventilation machines.

There is also included on the respiratory tube (205) a grooved recess (261) which is placed on the inside curve of the respiratory tube (205). This grooved recess (261) allows for the inflation tube (407) to be placed in more defined contact with the respiratory tube (205) and also be connected to the shield (201) via the second airtight seal (705). As shown in FIG. 1, the inflation tube (407) will generally be adhered to the respiratory tube (205) at the groove (261) and will extend along the respiratory tube (205) a predetermined distance through the second seal (705).

Figure 2:
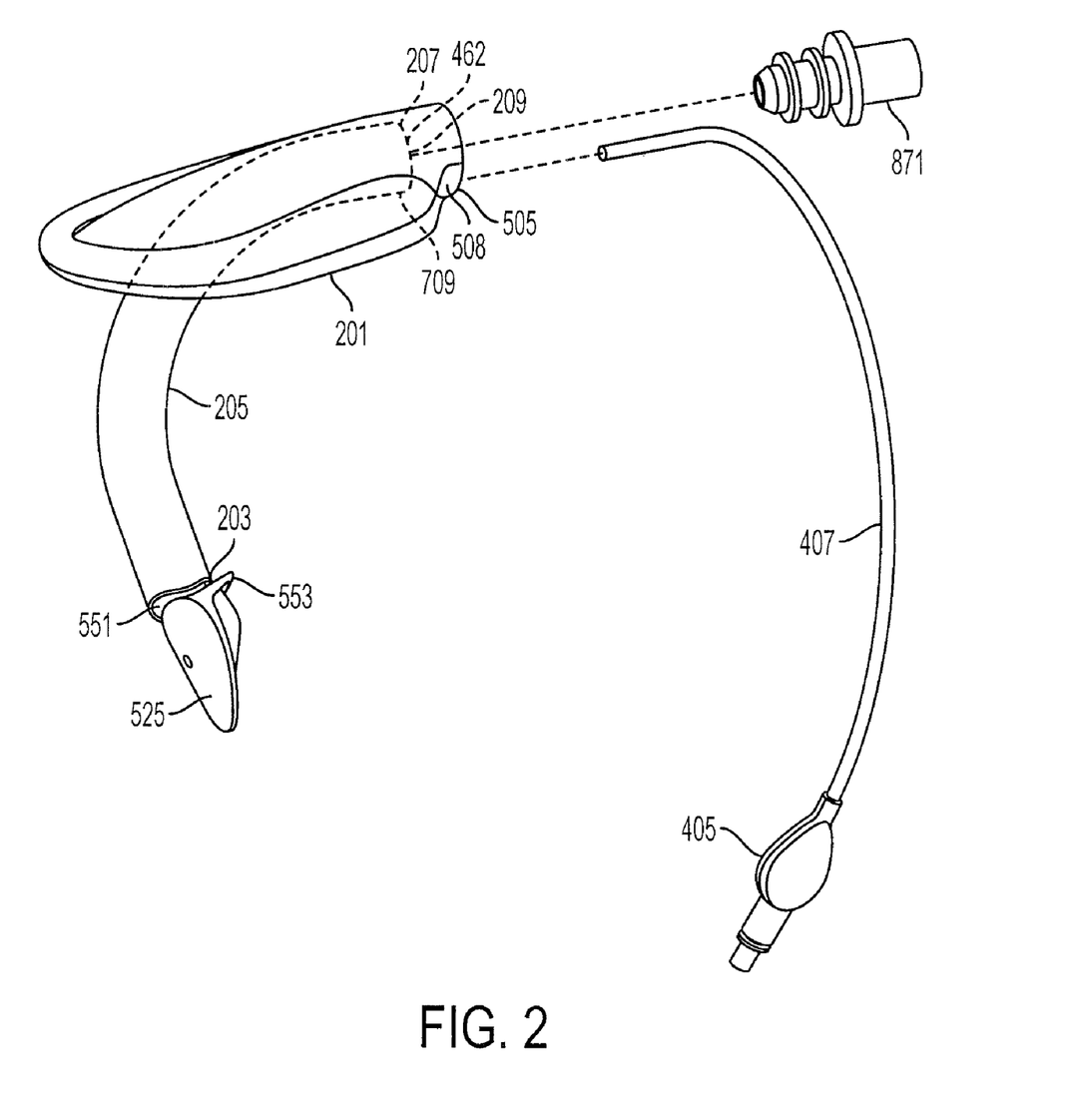
FIG. 2 shows a partially exploded view of the embodiment of FIG. 1 to show the manner of assembly.
Figure 5:
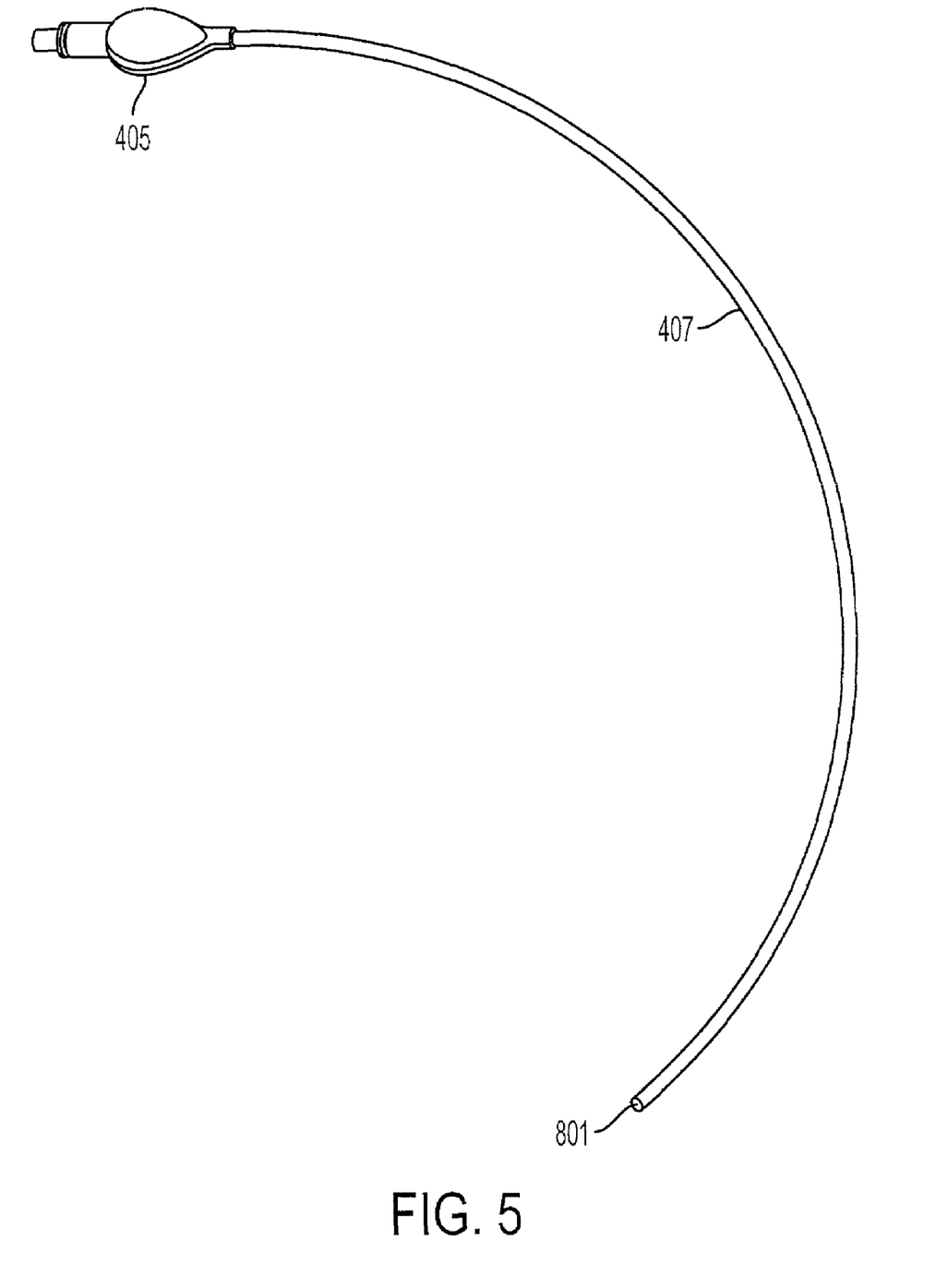
FIG. 5 shows a perspective view of an inflation pump and tube.

In order to assemble the mask (100), it is generally preferred that the following steps be performed to assemble the components, generally as indicated in FIG. 2. First the components are formed as shown in FIGS. 3-5. The shield (201), in FIG. 3 will be trimmed to remove the connection nozzle (461) and has a hole (709) cut through the proximal wall of the recess (511) as shown in FIG. 6. As should be apparent from FIGS. 3 and 6, the entry point (462) and hole (709) therefore present a relatively straight passage which extends from inside the recess (511) through the outer ring (401) and out the proximal end (505). There is also generally formed a connection recess (435) in the posterior base (403). This may be cut out or may be formed by simple compression of the material forming the posterior base (403).

The respiratory tube (205) is now inserted, proximal end (207) first, through the hole (709), passed through the outer ring (401), and extended out the entry point (462) and thus the posterior end (505) of the shield (201). The hole (709) and posterior end (505) are preferably sized and shaped to be of relatively similar size to the exterior diameter of the respiratory tube (205) so that a tight connection is formed by the respiratory tube (205) distending the material of the shield (201) slightly in both places. The respiratory tube (205) will continue to be slid through the hole (709) and posterior end (505) until the hole (709) interacts with the groove (551) and disk (553). At that point, the wedge (501) and disk (553) will generally be the only portions of the respiratory tube (205) which has not passed through the hole (709) and the reinforced support (525) will be adjacent to the recess (435) in the posterior base (403).

These pieces will then be connected together resulting in the wedge (501) being positioned in the recess (511) and generally flush with the interior of the posterior base (403). The connection between the posterior base (403) and the reinforced support (525) may be formed in any manner known to one of ordinary skill in the art, however, in a preferred embodiment, the two devices are adhered together with a generally non-separable adhesive. The respiratory tube (205) now is arranged to generally pass through the outer ring (401) in such a fashion as to form a first airtight seal (703) and a second airtight seal (705) which inhibit air in the outer ring (401) from entering the respiratory tube (205) and vice-versa.

In the depicted embodiment, the disk (553) and groove (551) formed toward the distal end (203) of the respiratory tube (205) serve to further reinforce the first airtight seal (703). In particular, the material surrounding the hole (709) will end up being stretched by the passing of the respiratory tube (205) until the hole (709) is aligned with the groove (551). The material will then relax and the hole (709) will collapse slightly into the groove (551). This provides a first level of sealing. The disk (553) adjacent to the hole (709) can then be provided with an adhesive which adheres to the shield (201) forming the airtight seal (703).

At the proximal end (505) of the shield (201), once the respiratory tube (205) is in position, the distal end (801) of the inflation tube (407) can be positioned to extend through the recessed groove (261) so that the distal end (801) is placed into the outer ring (401). The proximal end (505) of the shield (201) is then also provided with an adhesive in the neck (508) to form a second airtight seal between all of the respiratory tube (205), the inflation tube (407), and the proximal end (505) of the shield (201).

As should be apparent, once assembled the two airtight seals (703) and (705) serve to isolate the interior of the outer ring (401) from the interior of the respiratory tube (205). There is preferably no air transmission between these two devices. Further, as the distal end (801) of the inflation tube (407) is within the outer ring (401), and also sealed from the respiratory tube (205) and the outside air, the pump (405) can be used to provide or remove air into the outer ring (401). This results in its inflation or deflation as desired. The respiratory tube (205) provides for an opening from within the recessed cavity (511) of the shield (201), through the interior of the respiratory tube (205). This allows for a patient to breath through the respiratory tube (205) once it is in position. The removable connector (871) may also then be attached to the proximal end (207) of the respiratory tube (205) if desired.

This construction provides for a number of advantages. As should be apparent from the FIGS. and the above discussion, since the wedge (501) is originally attached to the respiratory tube (403) and is not formed as a portion of the shield (201) (such as it is for instance in U.S. patent application Ser. No. 10/691,399), the mold (901) is generally simpler as there is only a need for a single void into which the material of the shield (201) is placed. Further, the ability to eliminate the wedge (501) as a part of the shield (201) provides the ability to blow mold the shield (201) as discussed.

The assembly is still very simple, as the passage of the respiratory tube (403) through the structure of the inflatable outer ring (401) is accomplished by utilizing the structure of the respiratory tube (403) passing through the outer ring (401) via the hole (703) and posterior end (505). This provides for air isolation between the outer ring (401) and respiratory tube (403) without the need to mold walls or other structure for such isolation into the shield (201).

While in the above embodiment as depicted in FIG. 2, the proximal end (207) of the respiratory tube is first threaded through the hole (703) and posterior end (505), in an alternative embodiment, the wedge (501) and respiratory tube (403) may actually be inserted in the opposing direction to the embodiment shown in FIG. 2. In this alternative embodiment, the wedge section and the distal end (203) of the respiratory tube (205) would be first inserted through the posterior end (505), run through the outer ring (401), and exit the hole (703). While this method is viable in most cases, it is generally not preferred as it is usually more difficult to perform. Further, in some embodiments, it may require redesign of the wedge section components (such as the wedge (501), disk (553), or reinforced support (525)) to prevent damage to the hole (703) and posterior end (505) during the wedge passing through those structures.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of constructing a shield for a laryngeal mask airway; the method comprising:

providing an ovalized tool having two points of ovalization which interacts with a mold for a shield of a laryngeal mask airway, said mold including a hollow chamber for forming said shield;

aligning said ovalized tool so that said two points are arranged to feed material to portions of said hollow chamber which correspond to at least a portion of a posterior base of a shield;

blow molding said shield, said shield comprising an inflatable outer ring formed of a single layer of material and a posterior base formed of at least a double layer of material, each of said layers of said double layer of material being thicker than said single layer of material in said inflatable outer ring; and cutting a hole through a portion of said outer ring adjacent said posterior base.

2. The method of claim 1 wherein said shield further includes a connection nozzle on said proximal end, which is removed and discarded.

3. The method of claim 1 wherein said shield is intended to be disposed of after a single use.

4. The method of claim 1 wherein said hole is sized and shaped to allow a respiratory tube to pass therethrough.

5. A method for constructing a shield for a supraglottic airway; the method comprising:

providing an ovalized tool having two points of ovalization which interacts with a mold for a shield of a laryngeal mask airway, said mold including a hollow chamber for forming said shield, said tool producing a wall thickness in at least one first portion that is thicker than a wall thickness in a second portion;

aligning said ovalized tool so that said two points are arranged to feed material to portions of said hollow chamber which correspond to at least a portion of a posterior base of a shield; and blow-molding said shield of said supraglottic airway as a monolithic piece using said ovalized tool, said shield comprising an inflatable outer ring formed of a single layer of material and a posterior base formed of at least a double layer of material, each of said layers of said double layer of material being thicker than said single layer of material in said inflatable outer ring.

6. The method of claim 5 wherein said at least one first portion comprises at least two first portions.

7. The method of claim 5 wherein said supraglottic airway comprises a laryngeal mask.

8. The method of claim 5 wherein said shield further includes a connection nozzle on said proximal end, which is removed and discarded.

9. The method of claim 5 wherein said shield is intended to be disposed of after a single use.

10. The method of claim 5 wherein said shield is sized and shaped to attach to a respiratory tube.

11. The method of claim 10 wherein said shield is designed so that said respiratory tube passes through a portion of said shield.

12. The method of claim 6 wherein said at least two first portions are pressed together to form a posterior base of said shield and said second portion forms an inflatable outer ring of said shield.

* * * * *